United States Patent [19]

Belanger

[11] 4,076,939
[45] Feb. 28, 1978

[54] 2-(4-SUBSTITUTED-1,2,5-THIADIAZOLE-3-YLOXY)-ACETALDEHYDES

[75] Inventor: Patrice C. Belanger, Dollard des Ormeaux, Canada

[73] Assignee: Merck Sharp & Dohme (I.A.) Corporation, Rahway, N.J.

[21] Appl. No.: 766,637

[22] Filed: Feb. 8, 1977

Related U.S. Application Data

[63] Continuation-in-part of Ser. No. 602,720, Aug. 7, 1975, abandoned.

[51] Int. Cl.² .......................................... C07D 417/04
[52] U.S. Cl. .............................. 544/134; 260/268 H; 260/293.68; 260/302 D
[58] Field of Search ..................... 602/720; 544/134

[56] References Cited

U.S. PATENT DOCUMENTS

| | | | |
|---|---|---|---|
| 3,619,370 | 11/1971 | Weinstock et al. | 195/51 |
| 3,655,663 | 4/1972 | Wasson | 260/247.1 |
| 3,657,237 | 4/1972 | Weinstock et al. | 260/247.1 |

OTHER PUBLICATIONS

Allinger et al., "Organic Chemistry", Worth Publishers Inc., p. 455 (1971).

*Primary Examiner*—Henry R. Jiles
*Assistant Examiner*—R. W. Ramsuer
*Attorney, Agent, or Firm*—Daniel T. Szura; Rudolph J. Anderson, Jr.

[57] ABSTRACT

Novel 2-(4-substituted-1,2,5-thiadiazol-3-yloxy)acetaldehydes are disclosed. These acetaldehydes are useful as intermediates for preparing certain β-adrenergic blocking agents.

1 Claim, No Drawings

2-(4-SUBSTITUTED-1,2,5-THIADIAZOLE-3-YLOXY)-ACETALDEHYDES

CROSS REFERENCE TO RELATED APPLICATIONS

This application is a continuation-in-part of co-pending application Ser. No. 602,720, filed Aug. 7, 1975 now abandoned.

BACKGROUND OF THE INVENTION

Various methods of preparing β-adrenergic blocking agents of the 3-substituted-4-(3-amino-2-hydroxypropoxy)-1,2,5-thiadiazole type are known in the art. Such methods are disclosed in various United States Patents such as U.S. Pat. Nos. 3,657,237; 3,655,663 and 3,619,370.

Novel 1,2,5-thiadiazole aldehydes have been discovered. The aforesaid β-adrenergic blocking agents can be readily prepared from these novel aldehydes.

SUMMARY OF THE INVENTION

Novel 2-(4-substituted-1,2,5-thiadiazol-3-yloxy)-acetaldehydes.

PREFERRED EMBODIMENTS OF THE INVENTION

An embodiment of the present invention are substituted acetaldehydes having the formula

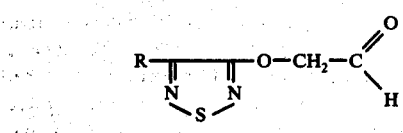
I wherein R is selected from $C_1-C_5$ alkyl, $C_1-C_5$ alkoxy, phenyl, benzyl and heterocyclic groups selected from morpholino, piperidyl, hydroxypiperidyl, N-loweralkylpiperazinyl, furyl, thienyl and pyrryl.

In a preferred embodiment R in Formula I is selected from the heterocyclic groups. A most preferred compound is Formula I wherein R is morpholino.

The compounds of Formula I can be conveniently prepared by oxidation of a compound having the formula

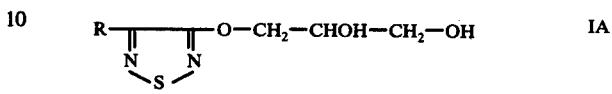
IA where R is as defined above. The Formula IA compounds may be prepared by a process analogous to that described in U.S. Pat. No. 3,850,045. Useful oxidizing agents are periodic acid and lead tetraacetate, with lead tetraacetate being preferred. This oxidation is carried out at temperatures ranging from −20° C. to 40° C., with about 25° C. being preferred. The oxidation is generally carried out in a suitable inert diluent. Water is conveniently used for the periodic acid system. A hydrocarbon such as benzene is an especially useful diluent for the lead acetate oxidation. The product aldehyde is recovered by conventional means.

The aldehydes of Formula I can be used as intermediates to prepare the corresponding 3-R-4(3-amino-2-hydroxypropoxy)-1,2,5-thiadiazoles. These thiadiazoles and their pharmaceutically acceptable salts are β-adrenergic blocking agents, as disclosed in U.S. Pat. No. 3,655,663. The preparation of the thiadiazoles can be accomplished by converting the aldehyde (I) to a nitro compound, catalytically hydrogenating the nitro compound to the corresponding amino compound and finally converting the amine to the desired alkylamino derivative. The reaction sequences are illustrated by the following equations:

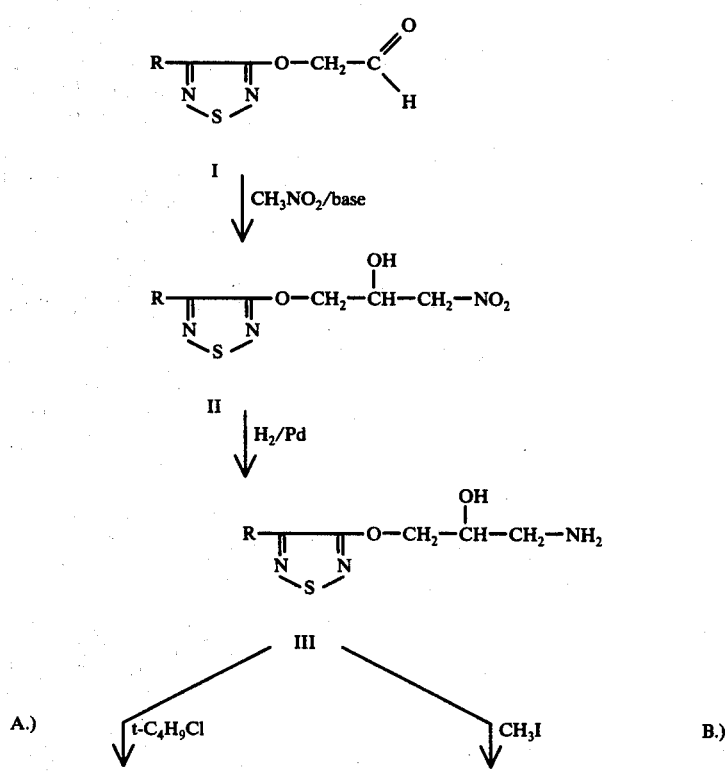

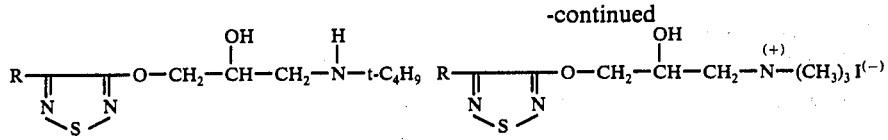

IV      III A

-continued

III A ↓ Base

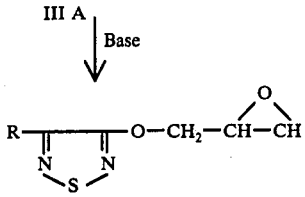

III B ↓ t-C₄H₉—NH₂

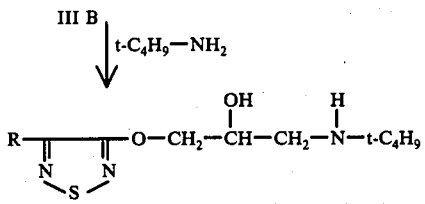

IV

Of the two routes A.) and B.) to the secondary amine IV, route B.) is preferred.

The following examples illustrate the preparation of acetaldehydes of Formula I. All parts are by weight unless otherwise indicated.

EXAMPLE 1

Periodic Acid Oxidation

Step A: 3-Morpholino-4-chloro-1,2,5-thiadiazole (1 g., 5 mmole), 2,2-dimethyl-1,3-dioxolan-4-yl methanol (0.7 g., 5 mmole) were heated under reflux for 2 hours in t-butanol containing potassium t-butoxide (0.7 g.). The reaction mixture was diluted with water (10 ml.) and extracted twice with ethyl acetate. After washing with water and drying over magnesium sulfate, evaporation provided 1.35 g. (90%) of (3-morpholino-1,2,5-thiadiazol-4-yloxy)-2,2-dimethyl-1,3-dioxolanyl methane in the form of a yellow oil.

Step B: 0.9 g. (3 mmole) of the [3-(3-morpholino-1,2,5-thiadiazol-4-yloxy)-2,2-dimethyl-1,3-dioxolanyl methane] was heated for 10 minutes in 1N hydrochloric acid (10 ml.). After a few minutes, a one-phase system was obtained. The solution was evaporated to dryness and a yellow oil, that slowly crystallized, was obtained which, following recrystallization from a mixture of petroleum ether-ethyl acetate provided 704 mg. of 3-(3-morpholino-1,2,5-thiadiazol-4-yloxy)-1,2-propanediol intermediate. This intermediate was recrystallized twice from the same solvent mixture, to provide a final product melting at 99° C.

Step C: 3-(3-Morpholino-1,2,5-thiadiazol-4-yloxy)-1,2-propanediol (261 mg., 1 mmole) was treated with sodium meta periodate (250 mg.) in water (5 ml.) and 1N hydrochloric acid (1 ml.) and then stirred at ambient temperature for 30 minutes. Extraction with ethyl acetate followed by the usual workup provided 0.22 g. (98%) of 2-(3-morpholino-1,2,5-thiadiazol-4-yloxy)acetaldehyde in the form of a yellow oil.

EXAMPLE 2

Lead Tetraacetate Oxidation 3-(3-Morpholino-1,2,5-thiadiazol-4-yloxy-1,2-propanediol (8.7 g; 33.3 mmoles) was treated with lead tetraacetate (15.5. g; 35 mmoles) in 100 ml benzene at ambient temperature for 4 hours. The solid was filtered off; the organic layer was washed twice with water, dried over magnesium sulfate and evaporated to dryness. A quantitative yield of 2-(3-morpholino-1,2,5-thiadiazol-4-yloxy)-acetaldehyde, in the form of a yellow oil, was obtained.

By replacing the 3-(3-morpholino-1,2,5-thiadiazol4-yloxy)-1,2-propanediol of Example 1 or 2 with an equivalent amount of 3-(3-ethyl-1,2,5-thiadiazol-4-yloxy)-1,2-propanediol, 3-(3-methoxy-1,2,5-thiadiazol-4-oxy)-1,2-propanediol, 3-(3-phenyl-1,2,5-thiadiazol-4-oxy)-1,2-propanediol, 3-(3-benzyl-1,2,5-thiadiazol-4-oxy)-1,2-propanediol, 3-[3-(3-methylpiperazinyl)-1,2,5-thiadiazol-4-oxy]-1,2-propanediol, 3-(3-piperidyl-1,2,5-thiadiazol-4-oxy)-1,2-propanediol, 3-[3-(4-hydroxypiperidyl)-1,2,5-thiadiazol-4-oxy]-1,2-propanediol, 3-[3-(2-furyl)-1,2,5-thiadiazol-4-oxy]-1,2-propanediol, 3-[3-thienyl-1,2,5-thiadiazol-4-oxy]-1,2-propanediol or 3-[3-(3-pyrryl)-1,2,5-thiadiazol-4-oxy]-1,2-propanediol, the corresponding substituted acetaldehydes are prepared.

What is claimed is:

1. Compounds having the formula:

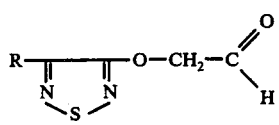

wherein
R is morpholino.

* * * * *